United States Patent [19]
Suzuki et al.

[11] Patent Number: 5,600,699
[45] Date of Patent: Feb. 4, 1997

[54] PANORAMIC X-RAY IMAGING APPARATUS

[75] Inventors: Masakazu Suzuki; Keisuke Mori; Akifumi Tachibana; Kazunari Matoba, all of Kyoto; Hitoshi Asai; Kazuhisa Miyaguchi, both of Hamamatsu, all of Japan

[73] Assignees: J. Morita Manufacturing Corporation, Kyoto; Hamamatsu Photonics Kabushiki Kaisha, Shizuoka, both of Japan

[21] Appl. No.: 598,442

[22] Filed: Feb. 8, 1996

[30] Foreign Application Priority Data

Feb. 9, 1995 [JP] Japan ..................................... 7-022148

[51] Int. Cl.$^6$ ..................................................... A61B 6/14
[52] U.S. Cl. ............................... 378/38; 378/40; 378/98.8
[58] Field of Search ............................... 378/38–40, 98.8

[56] References Cited

U.S. PATENT DOCUMENTS 4,878,234  10/1989  Pfeiffer et al. ............................. 378/40
4,995,062   2/1991  Schulze-Ganzlin et al. ............. 378/40

FOREIGN PATENT DOCUMENTS

57-31844    2/1982  Japan.
57-166144  10/1982  Japan.
60-163642   8/1985  Japan.
61-22841    1/1986  Japan.
2-84942     3/1990  Japan.
4-48169    11/1992  Japan.

Primary Examiner—Don Wong
Attorney, Agent, or Firm—Koda and Androlia

[57] ABSTRACT

The present invention provides a panoramic imaging apparatus capable of obtaining a clear tomographic image even when the rotation speed of a swivel member changes. The clock for driving an FFT CCD device in accordance with the TDI method is set on the basis of the angular speed ω of the arm detected by a tachogenerator and a function value f (θ) which responds to the rotation angle θ of the swivel member detected by an angle detector and used to determine a tomographic orbit. The angle detector is provided with a cam having a shape having been set in accordance with the relationship between the rotation angle θ and the film feeding speed at the time of performing X-ray panoramic imaging by using photographic films. The signal of the angular speed ω and the signal of the function value f (θ) corresponding to the angle θ are added by an analog multiplier, and subjected to frequency modulation by a V/F converter to create a TDI clock.

7 Claims, 7 Drawing Sheets

PANORAMIC X-RAY IMAGING APPARATUS

BACKGROUND OF THE INVENTION

1. Field of the Invention

The present invention relates to a panoramic X-ray imaging apparatus for performing tomographic imaging of the entire jaws of a human head for the purpose of dental diagnosis and treatment.

2. Description of the Related Arts

As related art of an X-ray imaging apparatus for performing tomographic imaging of the entire jaws of a human head for the purpose of dental diagnosis and treatment, prior art wherein the feeding speed of an X-ray film is adjusted is, for example, disclosed in Japanese Laid-open Patent Application No. Sho 57-31844. Japanese Laid-open Patent Application No. Sho 60-163642 discloses that the feeding speed of an X-ray film is adjusted in accordance with the curvature of a dental arch. Japanese Laid-open Patent Application No. Sho 57-166144 discloses prior art wherein X-rays are detected by using an X-ray image sensor, such as a CCD, and electrical image processing is performed, and then an image is displayed. Japanese Laid-open Patent Application No. Sho 61-22841 discloses prior art wherein an X-ray image formed on a CCD sensor while being moved is subjected to time delay integration in accordance with the movement by technology referred to as "Time Delay Integration (TDI)."

Furthermore, Japanese Utility Model Publication No. Hei 4-48169 and Japanese Laid-open Patent Application No. Hei 2-84942 disclose prior art wherein panoramic tomographic imaging of the jaws of a patient is performed by driving a CCD sensor by using the TDI method. In these references, an X-ray CCD sensor is used instead of an imaging film adapted to a conventional panoramic X-ray apparatus. In other words, at both ends of a horizontal arm which is rotatable around its vertical axis, an X-ray source and a CCD sensor are disposed opposite to each other with the head of a patient positioned between them. The X-ray beam generated from the X-ray source is narrowed by a primary slit and passes through the head of the patient, and is then narrowed by a secondary slit. The X-ray image at the secondary slit is converted into a visible light image and enters the CCD sensor. Signal charges are stored while the delay time of a vertical transfer clock signal for shifting at vertical shift registers is adjusted in accordance with the movement of the image at the secondary slit. As a result, a desired tomographic image by the TDI method can be obtained.

In Japanese Utility Model Publication No. Hei 4-48169 and Japanese Laid-open Patent Application No. Hei 2-84942, the adjustment of the vertical transfer clock signal of the CCD sensor by the TDI method is controlled by an internal CPU. However, the relationship between the clock signal and arm rotation is not disclosed. Accordingly, in these references, it is assumed that the arm rotates at a constant rotation speed and that film feeding speed is set in accordance with the rotation speed.

In case arm rotation is completely independent of the vertical transfer clock signal of the CCD sensor, when the rotation speed of the arm is changed by an unexpected problem while a panoramic X-ray image is taken, the relationship between arm rotation and the vertical transfer clock signal is deviated from a desired relationship, and no clear tomographic image can be obtained. In addition, a slow start function is desired to be added at the start of arm rotation in consideration of the safety of patients and the stability of the apparatus itself. Even when the slow start function is added, unless arm rotation speed is synchronous with the vertical transfer clock signal of the CCD sensor, no clear tomographic image can be obtained. Furthermore, the arm rotation speed may have variations inherent in the apparatus and may change with time. Moreover, the intensity of the X-rays from the X-ray source has upper and lower limits, and the intensity of the X-rays allowed to be applied to a human body is limited. For these reasons, when panoramic X-ray imaging is performed for a patient with a large head, it is necessary to perform imaging at low speed by taking longer time even when the intensity of the X-rays of the X-ray source is at its upper limit. When panoramic X-ray imaging is performed for a patient with a small head, it is necessary to lower the intensity of X-rays and perform imaging by taking shorter time at low X-ray intensity.

SUMMARY OF THE INVENTION

The purpose of the present invention is to provide a panoramic X-ray imaging apparatus capable of obtaining a desired tomographic image even when the rotation speed of a swivel member is changed because of unexpected problems and variations inherent in the apparatus.

The invention discloses a panoramic X-ray imaging apparatus provided with an X-ray generating means and an X-ray CCD detecting means disposed opposite to each other at both ends of a swivel member so as to perform tomographic imaging of the entire jaws of a human head positioned between the X-ray generating means and the X-ray CCD detecting means by driving the X-ray CCD detecting means in accordance with the TDI method, comprising:

an angle detecting means for detecting the rotation angle $\theta$ of the swivel member;

an angular speed detecting means for detecting the rotational angular speed $\omega$ of the swivel member; and a function generating means for generating a signal responding to the swivel member angle $\theta$ detected by the angle detecting means and representing a function value $f(\theta)$ used to determine a tomographic orbit, wherein a TDI clock for driving the X-ray CCD detecting means is derived by using a frequency determined on the basis of the angular speed $\omega$ detected by the angular speed detecting means and the function value $f(\theta)$ generated by the function generating means.

In the invention, the swivel member is provided with a sliding center mechanism which moves the rotation center of the swivel member so that X-ray irradiation is substantially vertical to a dental arch, and the function value $f(\theta)$ is compensated for the change in the position of the rotation center.

In the invention, the speed v for driving the X-ray CCD detecting means in accordance with the TDI method is set by the equation described below by using the function value $f(\theta)$, the rotational angular speed $\omega$ and constant k.

[Equation 2]
$$v = f(\theta) \times \omega \times \frac{1}{k}$$

In the invention, the angular speed detecting means detects the angular speed w by differentiating the angle $\theta$ detected by the angle detecting means.

In the invention, the angular speed detecting means detects the angle $\theta$ by integrating the angular speed detected by the angular speed detecting means.

In accordance with the invention, the X-ray generating means is disposed at one end of the swivel member and the X-ray CCD detecting means is disposed at the other end of the swivel member with the human head positioned between the X-ray generating means and the X-ray CCD detecting means. The X-ray CCD detecting means is driven by a clock frequency determined on the basis of the function value f (θ) of the rotation angle θ preset by the function generating means and the rotational angular speed ω so as to perform panoramic imaging in accordance with the TDI method. Since the clock frequency of the TDI method corresponds to the rotation angle θ of the swivel member, a clear tomographic image can be obtained while satisfying the human head conditions which are not always uniform. In particular, at the front portion or the like of a dental arch, wherein the rotation speed is reduced because the intensity of X-rays is attenuated by the presence of the cervical vertebrae or the like, the storage time of the image taken by the X-ray CCD detecting means can be prolonged, thereby producing a satisfactory image. In addition, even when smooth start and stop is performed by acceleration/deceleration control at the start and stop of the rotation, the imaging operation can sufficiently respond to the speed change, thereby producing a clear tomographic image.

Furthermore, in accordance with the invention, the swivel member is provided with the sliding center mechanism, and the drive of the X-ray CCD detecting means in accordance with the TDI method is compensated for the positional change of the rotation center, thereby producing an easy-to-diagnose panoramic X-ray image.

Furthermore, in accordance with the invention, since the speed v for driving the X-ray CCD detecting means in accordance with the TDI method is set on the basis of the product of the function value f (θ) and the angular speed ω of the swivel member, the speed can be set promptly and easily by using the function values f (θ) listed on a table or the like on the basis of data having been obtained and proven by using known panoramic tomographic imaging technology in which X-ray imaging films are used.

Furthermore, in accordance with the invention, since the angular speed ω is detected by differentiating the rotation angle θ, the angle sensor can be used as the angular speed sensor.

Furthermore, in accordance with the invention, since the rotation angle θ is detected by integrating the angular speed ω, the angle detecting means can be used as the angular speed detecting means.

Furthermore, in accordance with the invention, since the clock signal frequency for driving the X-ray CCD detecting means in accordance with the TDI method is set on the basis of the rotation angle θ and the angular speed ω of the swivel member, a satisfactory tomographic image can be obtained, even when the rotation speed of the swivel member is changed because of an unexpected problem or variations inherent in an apparatus.

Furthermore, in accordance with the invention, since the swivel member is provided with the sliding center mechanism and the clock frequency for the TDI method is compensated for the change in the position of the rotation center, an X-ray tomographic image can be obtained at a desirable geometric position along the entire circumference of a curved dental arch.

Furthermore, in accordance with the invention, the optimal drive speed v for the TDI drive can be obtained easily by preparing tabulated function values f (θ) by using known panoramic tomographic imaging technology in which X-ray imaging films are used.

Furthermore, in accordance with the invention, since the angular speed ω is obtained by differentiating the rotation angle θ, the detecting means for the rotation of the swivel member can be unified, thereby allowing to simplify the processing.

Furthermore, in accordance with the invention, since the rotation angle θ is obtained by integrating the angular speed ω, the detecting means for the rotation of the swivel member can be unified, thereby allowing to simplify the processing.

BRIEF DESCRIPTION OF THE DRAWINGS

Other and further objects, features, and advantages of the invention will be more explicit from the following detailed description taken with reference to the drawings wherein.

DETAILED DESCRIPTION OF THE PREFERRED EMBODIMENTS

Now referring to the drawings, preferred embodiments of the invention are described below.

Figure 1:
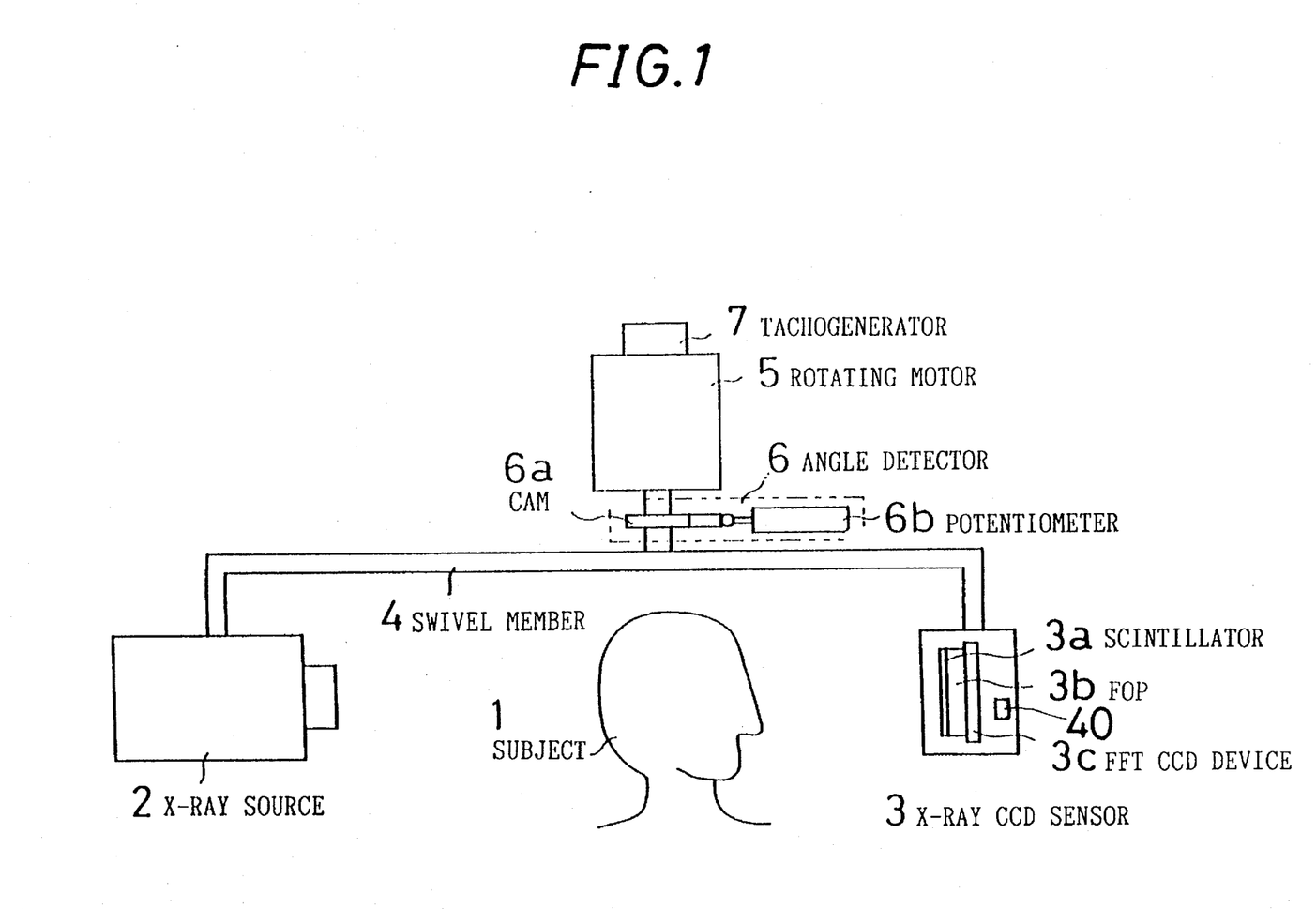
FIG. 1 is a front schematic view showing an arrangement condition in accordance with an embodiment of the invention.
Figure 2:
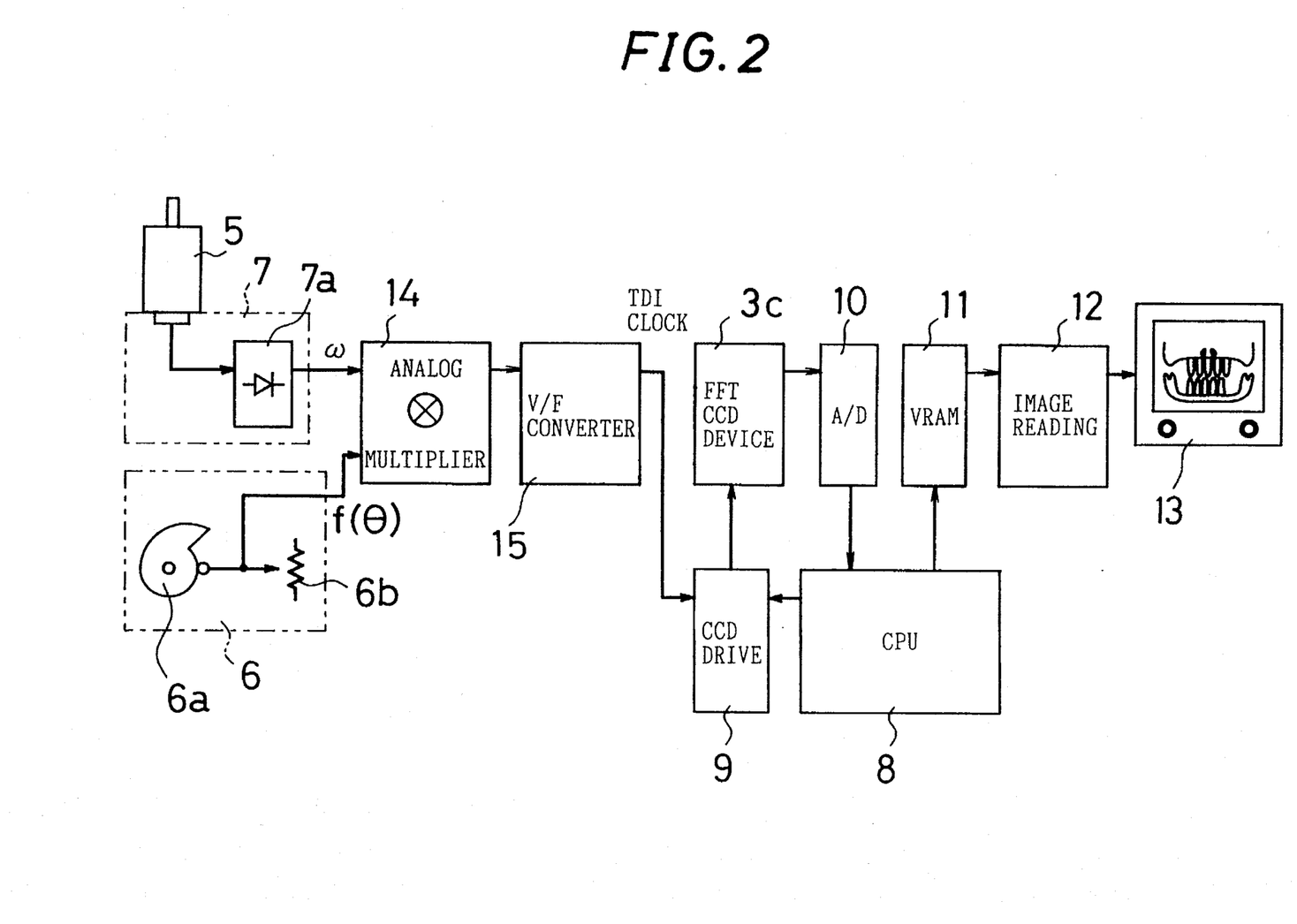
FIG. 2 is a block diagram showing an electrical configuration of the embodiment shown in FIG. 1.
Figure 3A:
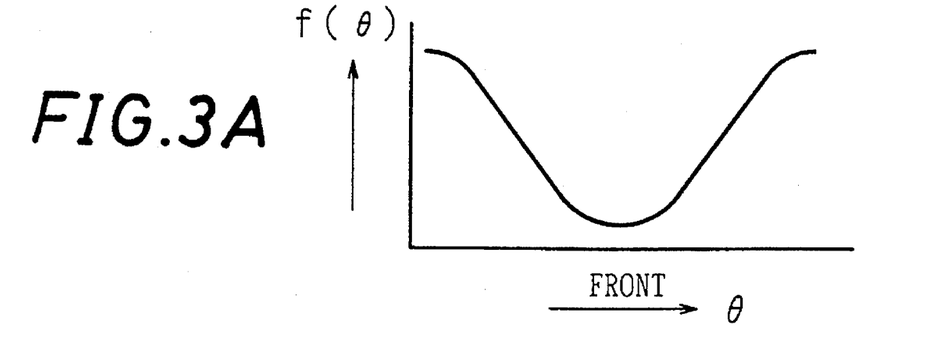
FIGS. 3a, 3b and 3b are graphs showing the operations of the embodiment shown in FIG. 1.
Figure 3B:
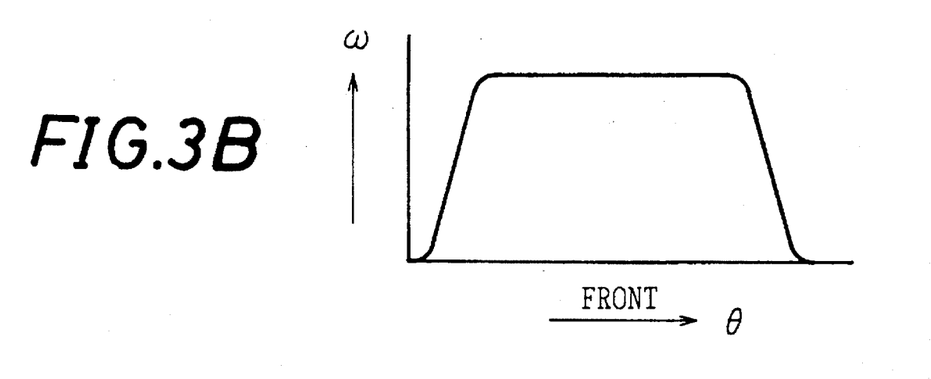
Figure 3C:
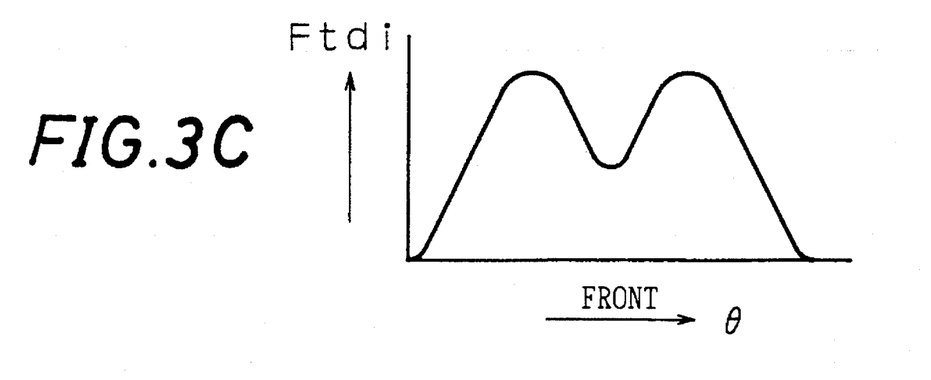
Figure 4:
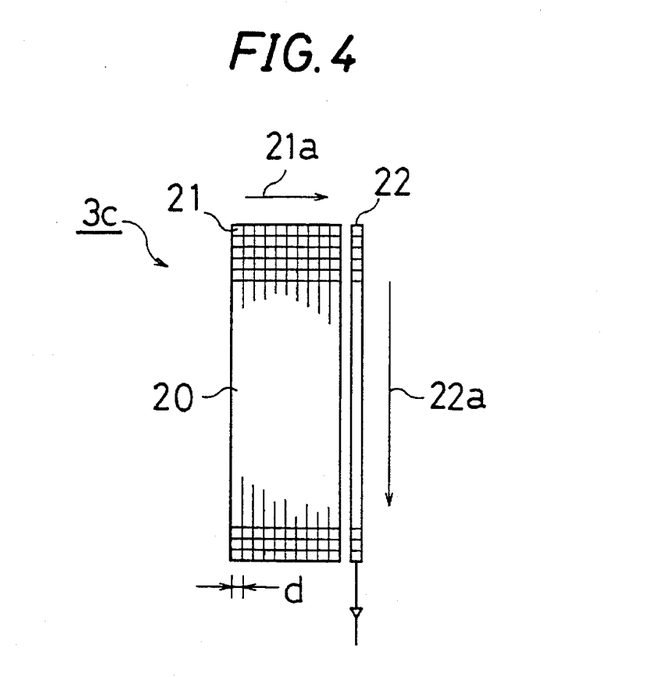
FIG. 4 is a schematic front view showing the operation principle of the FFT CCD device of the embodiment shown in FIG. 1.
Figure 5:
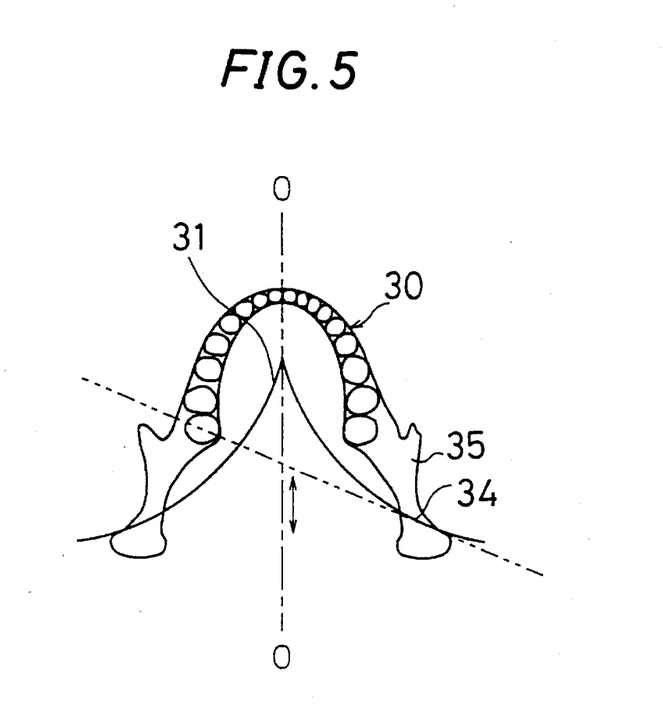
FIG. 5 is a schematic view showing the principle of a sliding center for accurately imaging a dental arch by using the embodiment shown in FIG. 1.
Figure 6A:
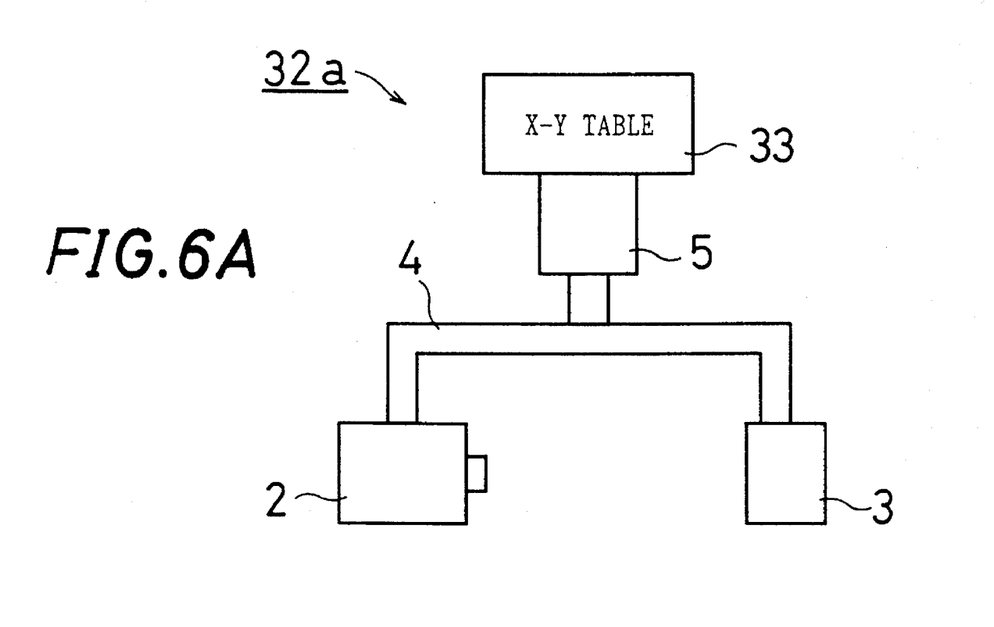
FIGS. 6a and 6b are schematic front views showing the examples of mechanisms for attaining the sliding center in the embodiment shown in FIG. 1.
Figure 6B:
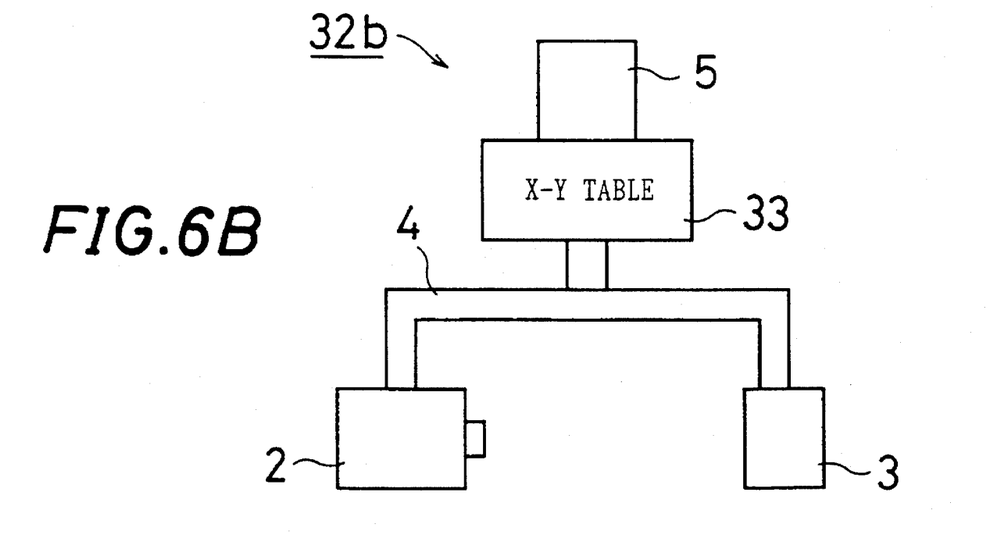

FIG. 1 shows an arrangement condition in accordance with an embodiment of the invention; FIG. 2 shows the electrical configuration of the embodiment shown in FIG. 1; FIGS. 3a, 3b and 3c show TDI clock frequency setting processes; FIG. 4 shows the fundamental configuration of a CCD sensor of a full frame transfer type (hereinafter referred to as "FFT") for X-ray detection; FIG. 5 shows the fundamental principle of a sliding center; and FIGS. 6a and 6b show configurations to attain the sliding center.

As shown in FIG. 1, a subject 1, such as a human head, is placed in the X-ray irradiation passage between an X-ray source 2 and an X-ray CCD sensor 3 disposed opposite to each other. The X-ray source 2 and the X-ray CCD sensor 3 are installed at both ends of a swivel member (such as a rotary arm) 4 which is rotatable. The X-ray CCD sensor 3 contains a scintillator 3a for converting applied X-ray into visible light, a fiber optic plate (abbreviated as "FOP") 3b for guiding an image taken by the scintillator 3a and an FFT CCD device 3c for taking the image guided by the optical fiber plate 3b. The swivel member 4 is rotated by a rotating motor 5. The rotation angle of the swivel member 4 is detected by an angle detector 6. The angle detector 6 comprises a cam 6a mounted on the rotation shaft of the rotating motor 5 and a potentiometer 6b, the movable contact of which is displaced by the cam 6a. The angular speed of the swivel member 4 is detected by a tachogenerator 7.

As shown in FIG. 2, the image taken by the FFT CCD device 3c is stored in accordance with the TDI method by a CCD drive circuit 9, the timing of which is controlled by a CPU 8. An image signal is converted into a digital signal by an analog/digital (hereinafter referred to as "A/D") converter 10 and supplied to the CFU 8. The CPU 8 writes the image signal in VRAM 11. The image written in the VRAM 11 is read by an image reading circuit 12 and displayed as a panoramic X-ray tomographic image by an image display apparatus 13.

The TDI clock for driving the FFT CCD device 3c is obtained by multiplying a signal representing the angular speed ω supplied from the tachogenerator 7 by a signal representing the function f (θ) of the angle θ supplied from the angle detector 6 by using an analog multiplier 14 and by performing frequency conversion by using a voltage/frequency (hereinafter referred to as "V/F") converter 15. The shape of the cam 6a of the angle detector 6 is set on the basis of the relationship between the rotation angle θ of the swivel member and the film feeding speed. The tachogenerator 7 is provided with a rectifier circuit 7a for converting a signal corresponding to the angular speed ω outputted as an alternating signal into a voltage level.

FIG. 3a shows an example of the function f (θ) of the angle θ, which is set as the shape of the cam 6a of the angle detector 6. The shape is determined by taking a sliding center function and a shadow problem elimination function. When v is a film feeding speed during panoramic imaging taken by using X-ray imaging films, and k is a constant, such a relationship as a first equation described below is obtained.

[Equation 3]
$$f(\theta) = \frac{v}{\omega} \times k \quad (1)$$

FIG. 3b shows an example of a change in the angular speed ω of the swivel member 4. Soft start processing wherein speed is changed gradually is performed at the start and stop of the rotation of the swivel member. FIG. 3c shows a change in the frequency Ftdi of the TDI clock, that is, the product of f (θ) and ω.

As shown in FIG. 4, in the FFT CCD device 3c, a vertical shift registers 21 of a two-dimensional matrix light-receiving portion 20 are arranged in a geometrically horizontal array direction 21a, that is, in a direction vertical to the longitudinal direction of a slender secondary slit. The X-ray tomographic image is converted into visible light by the scintillator 3a and guided onto the light-receiving portion 20 by the fiber optic plate 3b. The image corresponding to the X-ray tomographic image is moved in the array direction 21a as the arm 4 is rotated. When the TDI clock for shifting is supplied to the vertical shift registers 21 in accordance with the movement, a signal corresponding to the tomographic image is added up selectively. The added image signal is taken out by driving a horizontal shift register 22 in an array direction 22a by using a horizontal transfer clock.

When the vertical shift register 21 in the light-receiving portion 20 of the FFT CCD device 3c has a width d of one pixel in the array direction 21a, the clock frequency Ftdi is obtained by a second equation described below.

[Equation 4]
$$Ftdi = \frac{1}{k} \times f(\theta) \times \omega \div d \quad (2)$$

As shown in FIG. 5, a dental arch 30 has the shape of a nearly circular arc, although the shape is deformed considerably. By relatively moving the locus 31 of the rotation center of the swivel member 4 by using one of sliding center mechanisms 32a, 32b shown in FIGS. 6a, 6b, X-rays can vertically enter the dental arch 30, thereby affording a clear tomographic image. The configurations of the sliding mechanisms 32a, 32b are shown in FIGS. 6a, 6b, respectively. The mechanism is provided so as to displace the rotating motor 5 in a horizontal plane by using an X-Y table 33 or displace the X-Y table 33 for supporting the arm 4 by using the arm motor 5.

When using the sliding center function, the ratio of the distance between the center of rotation and each tooth in the dental arch 30 and the distance between each tooth and the X-ray CCD sensor 3 changes. In particular, at a portion near the medial line O—O of the human body, wherein the distance between the teeth and the center of rotation is small, the function value f (θ) is also set to a small value. Furthermore, when the locus 31 is as indicated by a solid line, the center of rotation is located at a position designated by numeral 34. When X-ray irradiation is performed as indicated by the imaginary line shown in FIG. 5, a shadow problem caused by a lower jaw branch 35 occurs. To solve this problem, it is necessary to change the locus 31. The detailed principle of changing the locus is disclosed in Japanese Laid-open Application No. Sho 60-163642 and more particularly in the lower left and lower right columns on page 2 of the specification thereof.

Figure 7A:
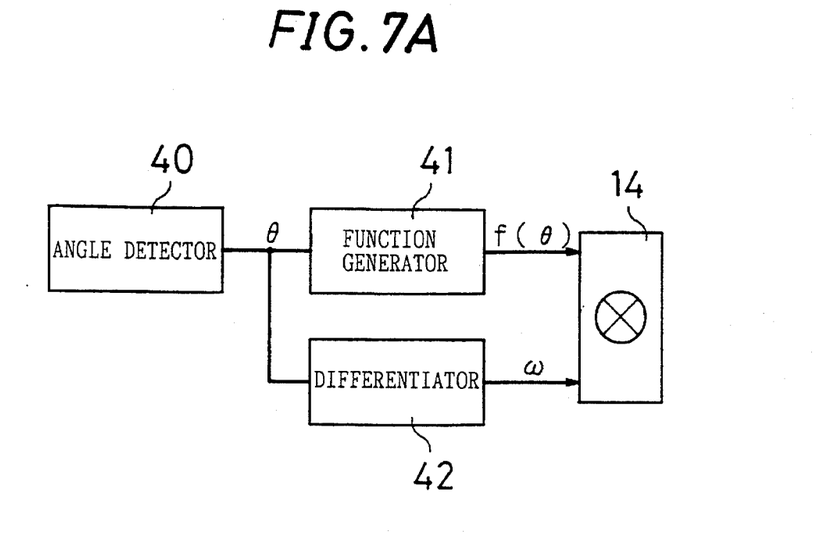
FIGS. 7a and 7b are block diagrams showing electrical configurations for detecting angular speeds and angles in other embodiments of the invention.
Figure 7B:
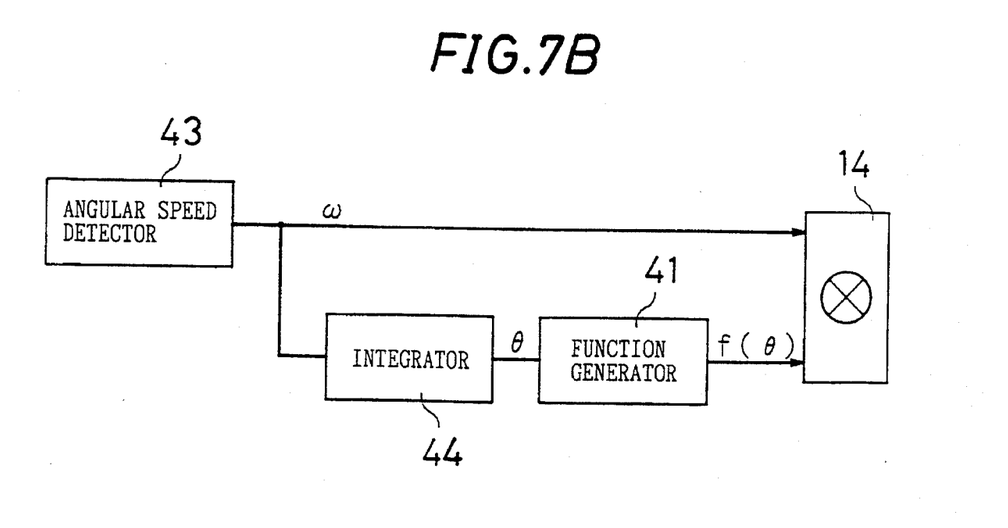

FIGS. 7a and 7b show configurations in accordance with other embodiments of the invention for converting the rotation angle θ or the angular speed ω by arithmetically operating one of the rotation angle θ and the angular speed ω by using the other. FIG. 7a shows a partial configuration, wherein a signal representing the rotation angle θ supplied from the angle detector 40 is converted into a signal representing the function value f (θ) by a function generator 41, and the signal is differentiated by a differentiator 42 to obtain a signal representing the angular speed ω. FIG. 7b also shows a partial configuration, wherein a signal representing the angular speed ω supplied from the angular speed detector 43, such as a tachogenerator, is converted into a signal representing the rotation angle θ by an integrator 44. Other elements following (downstream) the analog multiplier 14 are the same as those of the configuration shown in FIG. 2. When one of the angle θ and the angular speed ω is obtained, the other, that is, the angular speed ω or the angle θ, is obtained by electrical signal processing by using the differentiator 42 or the integrator 44. For example, the difference in the angle θ at each constant sampling period is obtained as a differential value, or the value of the angular speed ω at each constant sampling period is integrated and obtained as an integrated value.

Figure 8:
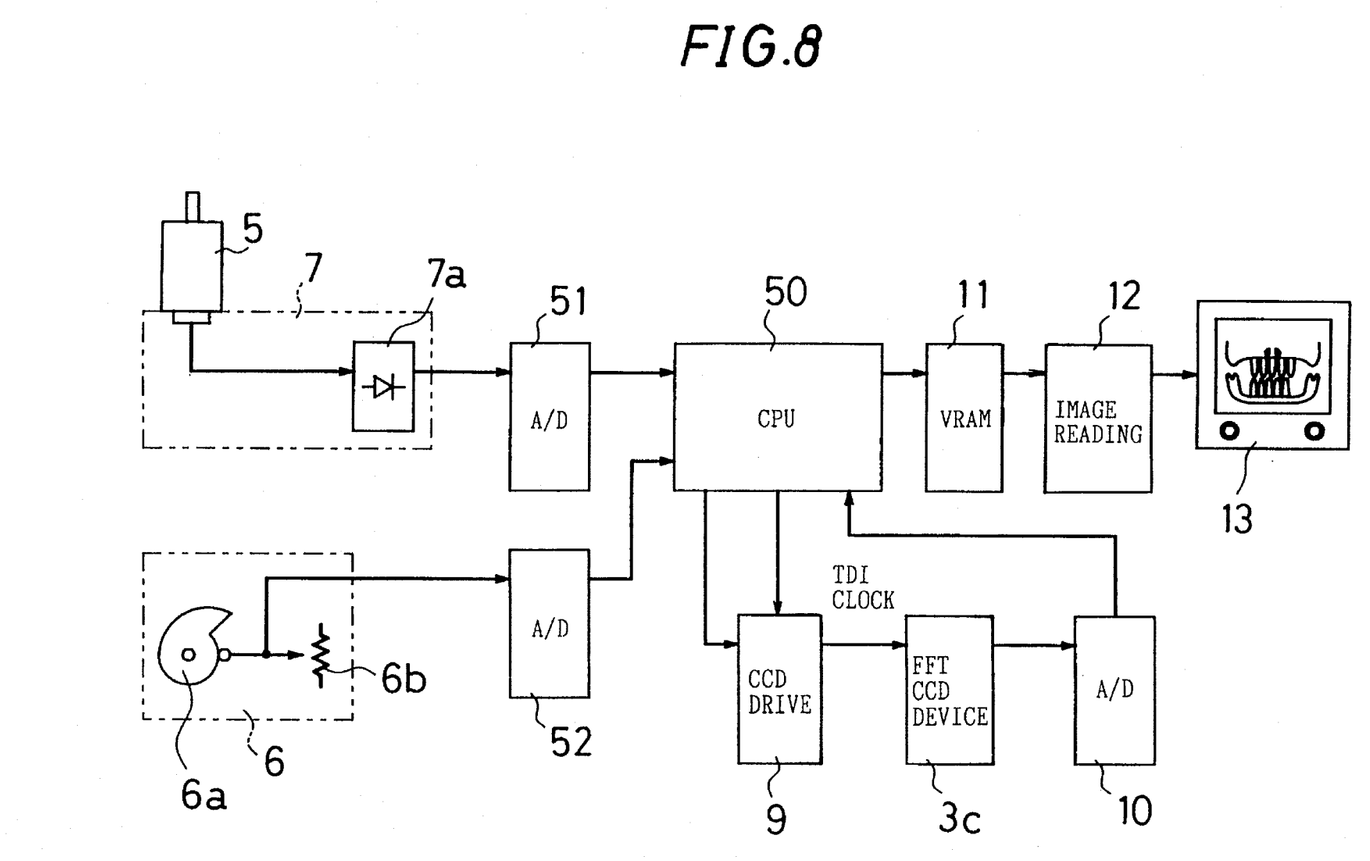
FIG. 8 is a block diagram showing an electrical configuration of still another embodiment of the invention.

FIG. 8 shows a configuration in accordance with still another embodiment of the invention for calculating the TDI clock frequency by the digital operation processing by using a CPU 50. The elements corresponding to those of the configuration shown in FIG. 2 are designated by the same reference numerals. In this embodiment, the function values f (θ) are set as tabulated data in the memory of the CPU 50. The outputs of the angle detector 6 and the tachogenerator 7 are converted digitally by A/D converters 51, 52 and supplied to the CPU 50. The CPU 50 performs the calculation of 1/k×f(θ)×ω/d in accordance with a preset program so as to perform processing and control for generating the TDI clock.

Although the thus-obtained X-ray panoramic tomographic image is shown on the image display apparatus 13 and used for dental diagnosis and treatment in the above-mentioned embodiments, the image can also be printed out easily by a printer or the like.

The invention may be embodied in order specific forms without departing from the spirit or essential characteristics thereof. The present embodiments are Wherefore to be considered in all respects as illustrative and not restrictive the scope of the invention being indicated by the appended claims rather than by the foregoing description and all changes which come within the meaning and the range of equivalency of the claims are therefore intended to be embraced therein.

What is claimed is:

1. A panoramic X-ray imaging apparatus provided with an X-ray generating means and an X-ray CCD detecting means disposed opposite to each other at both ends of a swivel member so as to perform tomographic imaging of the entire jaws of a human head positioned between the X-ray generating means and the X-ray CCD detecting means by driving the X-ray CCD detecting means in accordance with the TDI method, said apparatus comprising:

an angle detecting means for detecting the rotation angle θ of the swivel member;

an angular speed detecting means for detecting the rotational angular speed ω of the swivel member; and a function generating means for deriving a signal responding to the rotation angle θ detected by the angle detecting means and representing a function value f(θ) used determine a tomographic orbit, wherein a TDI clock driving the X-ray CCD detecting means is derived by using a frequency determined on the basis of the angular speed ω detected by the angular speed detecting means and the function value f(θ) generated by the function generating means.

2. The panoramic X-ray imaging apparatus according to claim 1, wherein the swivel member is provided with a sliding center mechanism which moves the rotation center of the swivel member so that X-ray irradiation is substantially vertical to a dental arch, and the function value f(θ) is compensated for the change in the position of the rotation center.

3. The panoramic X-ray imaging apparatus according to claim 1 or 2, wherein the speed v for driving the X-ray CCD detecting means in accordance with the TDI method is set by the following equation:

$$v = f(\theta) \times \omega \times \frac{1}{k}$$

wherein f(θ) and ω are as previously defined and k is a constant.

4. The panoramic X-ray imaging apparatus according to claim 1 or 2, wherein the angular speed detecting means detects the angular speed ω by differentiating the angle θ detected by the angle detecting means.

5. The panoramic X-ray imaging apparatus according to claim 1 or 2, wherein the angular speed detecting means detects the angle θ by integrating the angular speed ω detected by the angular speed detecting means.

6. The panoramic X-ray imaging apparatus according to claim 3, wherein the angular speed detecting means detects the angular speed ω by differentiating the angle θ detected by the angle detecting means.

7. The panoramic X-ray imaging apparatus according to claim 3, wherein the angular speed detecting means detects the angle θ by integrating the angular speed ω detected by the angular speed detecting means.

* * * * *

UNITED STATES PATENT AND TRADEMARK OFFICE
CERTIFICATE OF CORRECTION

PATENT NO.   : 5,600,699
DATED        : February 4, 1997
INVENTOR(S)  : Masakazu Suzuki, et al.

It is certified that error appears in the above-identified patent and that said Letters Patent is hereby corrected as shown below:

Title page,
Item [75] Inventors:  Change "Masakazu Suzuki; Keisuke Mori; Akifumi Tachibana; Kazunari Matoba, all of Kyoto; Hitoshi Asai; Kazuhisa Miyaguchi, both of Hamamatsu, all of Japan" to --Masakazu Suzuki; Keisuke Mori; Akifumi Tachibana; Kazunari Matoba, all of Kyoto; Hitoshi Asai; Kazuhisa Miyaguchi, both of Hamamatsu; Toshitaka Takeguchi, Ogasa, all of Japan--

Signed and Sealed this

Sixth Day of May, 1997

*Attest:*

*Attesting Officer*

BRUCE LEHMAN

*Commissioner of Patents and Trademarks*